(12) United States Patent
Urich et al.

(10) Patent No.: US 6,478,781 B1
(45) Date of Patent: Nov. 12, 2002

(54) ANTERIOR CHAMBER STABILIZING DEVICE FOR USE IN EYE SURGERY

(75) Inventors: Alex Urich, Mission Viejo, CA (US); Michael Curtis, Lake Forest, CA (US)

(73) Assignee: Circuit Tree Medical, Inc., Mission Viejo, CA (US)

( * ) Notice: Subject to any disclaimer, the term of this patent is extended or adjusted under 35 U.S.C. 154(b) by 0 days.

(21) Appl. No.: 09/546,804

(22) Filed: Apr. 11, 2000

(51) Int. Cl.⁷ .......................... A61M 5/00; A61M 25/00
(52) U.S. Cl. ............................ 604/264; 604/4
(58) Field of Search .......................... 604/27, 196, 4, 604/171, 43, 28, 264; 435/33

(56) References Cited

U.S. PATENT DOCUMENTS

| | | |
|---|---|---|
| 1,206,126 A | 11/1916 | Mitsch |
| 3,301,063 A | 1/1967 | Kisling, III et al. |
| 3,476,144 A | 11/1969 | Krantz |
| 3,501,959 A | 3/1970 | Womack |
| 3,661,144 A | 5/1972 | Jensen et al. |
| 3,784,039 A | 1/1974 | Marco |
| 3,812,855 A | 5/1974 | Banko |
| 3,863,504 A | 2/1975 | Borsanyi |
| 4,016,882 A | 4/1977 | Broadwin et al. |
| 4,077,845 A * | 3/1978 | Johnson ..................... 435/33 |
| 4,226,124 A | 10/1980 | Kersten |
| 4,382,442 A | 5/1983 | Jones |
| 4,395,258 A | 7/1983 | Wang et al. |
| 4,425,115 A | 1/1984 | Wuchinich |
| 4,457,455 A | 7/1984 | Meshberg |
| 4,465,470 A | 8/1984 | Kelman |
| 4,468,217 A | 8/1984 | Kuzmick et al. |
| 4,526,593 A | 7/1985 | Meyerson |
| 4,650,461 A | 3/1987 | Woods |
| 4,706,687 A | 11/1987 | Rogers |
| 4,722,350 A | 2/1988 | Armeniades et al. |
| 4,757,814 A | 7/1988 | Wang et al. |
| 4,770,654 A | 9/1988 | Rogers et al. |
| 4,808,154 A | 2/1989 | Freeman |
| 4,832,685 A | 5/1989 | Haines |
| 4,834,724 A * | 5/1989 | Geiss et al. ................. 604/280 |
| 4,838,281 A | 6/1989 | Rogers et al. |
| 4,838,853 A | 6/1989 | Parisi |
| 4,904,238 A * | 2/1990 | Williams ..................... 604/43 |

(List continued on next page.)

FOREIGN PATENT DOCUMENTS

| | | |
|---|---|---|
| EP | 0 251 694 B1 | 7/1988 |
| EP | 0 251 694 A2 | 7/1988 |
| EP | 0 284 322 A3 | 9/1988 |
| EP | 0 284 322 A2 | 9/1988 |
| EP | 0 284 322 B1 | 2/1993 |
| EP | 0 931 519 A1 | 7/1999 |
| WO | WO 88/10102 | 12/1988 |

Primary Examiner—Teresa Walberg
Assistant Examiner—Leonid M Fastovsky
(74) Attorney, Agent, or Firm—Irell & Manella, LLP

(57) ABSTRACT

An irrigation tube that has a relatively high fluidic resistance. The high resistance can be created by providing a relatively long tube. The aspiration tube and an irrigation tube may be coupled to an anterior chamber of a cornea during a phaco procedure. The high resistance of the tube will minimize the instantaneous change of flowrate out of the cornea in the event an occlusion is cleared from the aspiration tube. Minimizing the change in flowrate will tend to insure a higher flowrate from the irrigation line and a positive pressure within the cornea. The aspiration tube may have a plurality of pre-formed coils to minimize the effective length of the tube.

21 Claims, 1 Drawing Sheet

U.S. PATENT DOCUMENTS

| | | | |
|---|---|---|---|
| 4,935,005 A | | 6/1990 | Haines |
| 4,983,160 A | | 1/1991 | Steppe et al. |
| 5,024,654 A | * | 6/1991 | Tyler .............................. 604/4 |
| 5,111,971 A | | 5/1992 | Winer |
| 5,123,903 A | | 6/1992 | Quaid et al. |
| 5,152,746 A | | 10/1992 | Atkinson et al. |
| 5,167,725 A | | 12/1992 | Clark et al. |
| 5,188,102 A | | 2/1993 | Idemoto et al. |
| 5,197,485 A | | 3/1993 | Grooters |
| 5,282,786 A | | 2/1994 | Ureche |
| 5,312,329 A | | 5/1994 | Beaty et al. |
| 5,324,297 A | | 6/1994 | Hood et al. |
| 5,324,299 A | | 6/1994 | Davison et al. |
| 5,342,380 A | | 8/1994 | Hood |
| 5,354,265 A | | 10/1994 | Mackool |
| 5,354,268 A | | 10/1994 | Peterson et al. |
| 5,380,274 A | | 1/1995 | Nita |
| 5,391,144 A | | 2/1995 | Sakurai et al. |
| 5,403,276 A | | 4/1995 | Schechter et al. |
| 5,413,578 A | | 5/1995 | Zahedi |
| 5,454,784 A | | 10/1995 | Atkinson et al. |
| 5,464,389 A | | 11/1995 | Stahl |
| 5,520,652 A | | 5/1996 | Peterson |
| 5,527,292 A | * | 6/1996 | Adams et al. .............. 604/171 |
| 5,531,672 A | * | 7/1996 | Lynn .............................. 604/4 |
| 5,547,473 A | * | 8/1996 | Preyman ...................... 604/27 |
| 5,560,747 A | * | 10/1996 | McCue et al. ............... 604/196 |
| 5,582,588 A | | 12/1996 | Sakurai et al. |
| 5,591,127 A | | 1/1997 | Barwick, Jr. et al. |
| 5,628,743 A | | 5/1997 | Cimino |
| 5,630,939 A | | 5/1997 | Bulard et al. |
| 5,643,200 A | * | 7/1997 | Edwards ...................... 604/27 |
| 5,676,650 A | | 10/1997 | Grieshaber et al. |
| 5,685,840 A | | 11/1997 | Schechter et al. |
| 5,700,240 A | | 12/1997 | Barwick, Jr. et al. |
| 5,722,945 A | | 3/1998 | Anis et al. |
| 5,730,156 A | | 3/1998 | Mackool |
| 5,733,256 A | | 3/1998 | Costin |
| 5,743,871 A | | 4/1998 | Strukel et al. |
| 5,746,719 A | | 5/1998 | Farra et al. |
| 5,766,146 A | | 6/1998 | Barwick, Jr. |
| 5,807,310 A | | 9/1998 | Hood |
| 5,810,765 A | | 9/1998 | Oda |
| 5,817,099 A | | 10/1998 | Skolik et al. |
| 5,843,021 A | | 12/1998 | Edwards et al. |
| 5,890,516 A | | 4/1999 | Talamonti |
| 5,897,569 A | | 4/1999 | Kellogg et al. |
| 6,083,193 A | | 7/2000 | Kadziauskas et al. |
| 6,110,259 A | | 8/2000 | Schultz et al. |
| 6,179,803 B1 | | 1/2001 | Edwards et al. |
| 6,193,683 B1 | | 2/2001 | Ludin et al. |
| 6,203,540 B1 | | 3/2001 | Weber |

* cited by examiner

ANTERIOR CHAMBER STABILIZING DEVICE FOR USE IN EYE SURGERY

BACKGROUND OF THE INVENTION

1. Field of the Invention

The present application relates to an aspiration tube for a medical aspiration system.

2. Prior Art

The lens of a human eye may develop a cataracteous condition which affects a patients vision. Cataracteous lenses are sometimes removed and replaced in a procedure commonly referred to as phacoemulsification. Phaco procedures are typically performed with an ultrasonically driven handpiece which is used to break the lens. The broken lens is removed through an aspiration line that is coupled to the handpiece.

The handpiece has a tip which is inserted through an incision in the cornea. The handpiece typically contains a number of ultrasonic transducers that convert electrical power into a mechanical oscillating movement of the tip. The distal end of the tip has an opening that is in fluid communication with the aspiration line. The distal end of the tip also has a sleeve which has an opening in fluid communication with an irrigation line. The irrigation line is typically connected to a bottle that can provide irrigation fluid to the surgical site.

The oscillating movement of the tip will break the lens into small pieces. The lens pieces and irrigation fluid are drawn into the aspiration line through the opening of the tip. When performing a phaco procedure it is essential to maintain a positive pressure within the anterior chamber of the eye. A negative pressure may cause the cornea to collapse. To maintain a positive chamber pressure the system is configured to provide a flowrate through the irrigation tube that is greater than the flowrate through the aspiration tube.

It has been found that the aspiration tube may become occluded during a procedure. The occlusion will increase the vacuum pressure within the aspiration line. When the occlusion is cleared the anterior chamber may be instantaneous exposed to a high vacuum pressure. The vacuum pressure may cause the cornea to collapse. It would be desirable to provide an aspiration system that minimizes the effects of a cleared occlusion within an aspiration tube of the system.

BRIEF SUMMARY OF THE INVENTION

One embodiment of the present invention is an aspiration tube that has at least one pre-formed coil.

DETAILED DESCRIPTION OF THE PREFERRED EMBODIMENT

Figure 1:
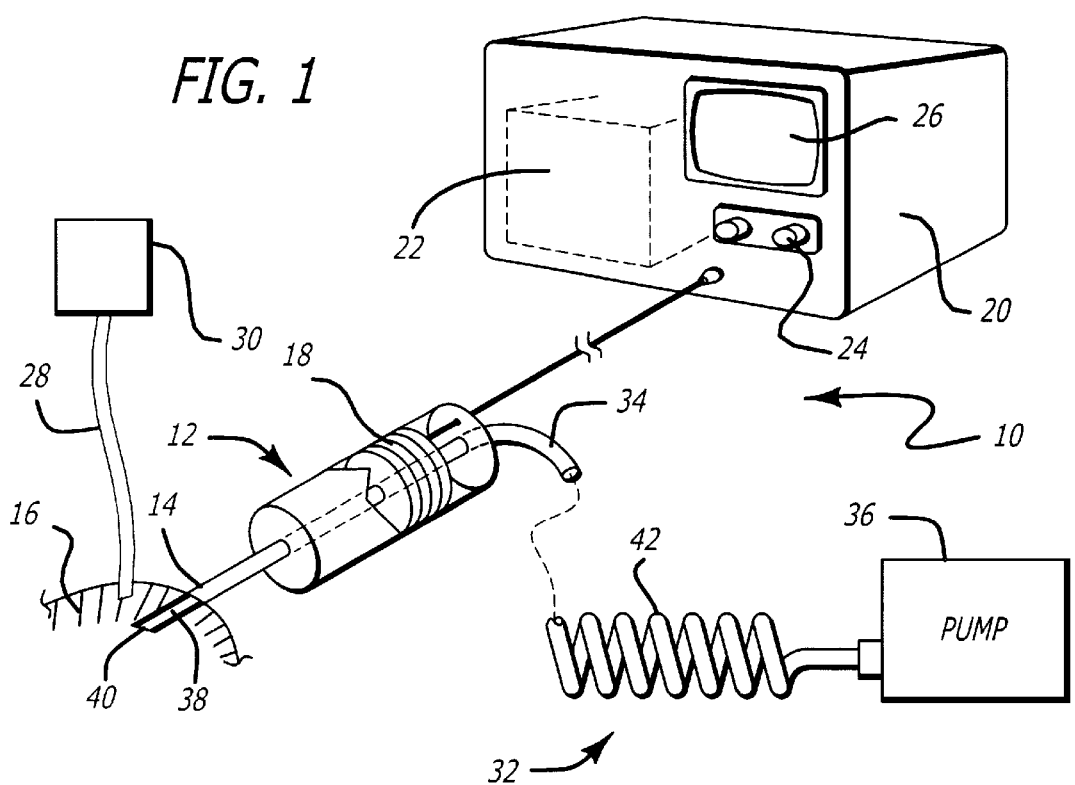
FIG. 1 is an illustration of a medical system which contains an aspiration tube that has a relatively high fluidic resistance.

In general the present invention includes an aspiration tube that has a relatively high fluidic resistance. The high resistance can be created by providing a relatively long tube. The aspiration tube and an irrigation tube may be coupled to an anterior chamber of a cornea during a phaco procedure. The high resistance of the aspiration tube will minimize the instantaneous change of flowrate out of the cornea in the event an occlusion is cleared from the tube. Minimizing the change in aspiration flowrate will insure a relatively higher flowrate from the irrigation line and a positive pressure within the cornea. The aspiration tube may have a plurality of pre-formed coils to minimize the effective length of the tube.

Referring to the drawings more particularly by reference numbers, FIG. 1 shows an embodiment of a medical system 10 of the present invention. The system 10 may include an ultrasonically driven handpiece which has a tip 14 that can be inserted into a cornea 16. The tip 14 may also be referred to as a cutting element. The handpiece 12 may include one or more ultrasonic transducers 18 that convert electrical power into mechanical movement of the tip 14. The handpiece 12 is typically held by a surgeon who performs a surgical procedure with the system 10. By way of example, the system 10 can be used to perform a phacoemulsification procedure to break and aspirate a lens of the cornea 16.

The handpiece 12 may be connected to a console 20 of the system 10. The console 20 may contain a control circuit 22 that provides a driving signal to the transducers 18. The console 20 may have input knobs or buttons 24 that allow the surgeon to vary different parameters of the system 10. The console 20 may also have a readout display 26 that provides an indication of the power level, etc. of the system 10.

The system 10 may include an irrigation tube 28 that is connected to an irrigation bottle 30. The irrigation tube 28 can be inserted into the cornea 16. The irrigation bottle 30 may contain an irrigation fluid that flows into the cornea 16 through the irrigation tube 28.

The medical system 10 may further have an aspiration system 32 that aspirates the irrigation fluid and broken lens out of the cornea 16. The aspiration system 32 may include an aspiration tube 34 that is connected to the handpiece 12 and a vacuum pump 36. The aspiration tube 34 is in fluid communication with an inner channel 38 and an opening 40 of the tip 14. The vacuum pump 36 creates a negative pressure within the aspiration tube 34 to induce a flow of irrigation fluid and emulsified tissue out of the cornea 16. The pump 36 is configured so that the flowrate through the irrigation tube 28 is slightly greater than the flowrate through the aspiration tube 34.

The aspiration tube 34 has a relatively large fluidic resistance to create a large fluid inertia in the aspiration system 32. The large inertia minimizes instantaneous changes in the flowrate of irrigation fluid through the aspiration tube 34. Thus if an occlusion is cleared within the aspiration tube 34 the large fluidic resistance will restrict the variation in aspiration fluid flow and minimize the probability of a cornea collapse event.

It has been found that having an aspiration tube 34 at least 8 feet long will provide a fluidic resistance sufficient to minimize the effects of an occlusion during a phaco procedure. A tube 34 less than 8 feet may not provide enough fluidic resistance to minimize changes in flowrate through the aspiration tube 34. The aspiration tube 34 may contain a plurality of pre-formed coils 42 to shorten the effective length of the tube 34. Coiling the aspiration tube 34 also increases the fluidic resistance of the tube 34.

In one embodiment the aspiration tube 34 may have a pre-coiled straight length of 12 feet. There may be 50 pre-formed coils 42, each having a diameter of 0.5 inches. The inner diameter of the tube 34 may be 0.065 inches. It has been found that such an embodiment will reduce the flowrate generated by a vacuum pressure of 600 millimeters of mercury (mmHg) approximately 10 times from a straight uncoiled tube of equal length.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

Although the pre-formed coils 42 are shown in a cylindrical "telephone cord" arrangement, it is to be understood that the coils 42 may be provided in a different configuration. For example, the coils 42 may be nested or overlapping.

What is claimed is:

1. An aspiration tube for a medical aspiration system, comprising:
   a tube that has at least one pre-formed coil that has a pre-coiled length of at least 8 feet.

2. The aspiration tube of claim 1, wherein said tube has at least approximately 50 coils.

3. The aspiration tube of claim 2, wherein each coil has a diameter of approximately 0.5 inches.

4. The aspiration tube of claim 1, wherein said tube has an inner channel with a diameter of approximately 0.06 inches.

5. An aspiration tube for a medical aspiration system, comprising:
   a tube that has a length of at least 8 feet.

6. A medical aspiration system, comprising:
   a pump; and,
   a tube that is connected to said pump, said tube has at least one pre-formed coil that has a pre-coiled length of at least 8 feet.

7. The aspiration system of claim 6, wherein said tube has at least approximately 50 coils.

8. The aspiration system of claim 7, wherein each coil has a diameter of approximately 0.5 inches.

9. The aspiration system of claim 6, wherein said tube has an inner channel with a diameter of approximately 0.06 inches.

10. A medical aspiration system, comprising:
    a pump; and,
    a tube that is connected to said pump, said tube has a length of at least 8 feet.

11. A medical cutting system, comprising:
    a handpiece;
    a cutting element attached to said handpiece;
    a tube that is connected to said handpiece and has at least one pre-formed coil that has a pre-coiled length of at least 8 feet; and,
    a pump connected to said tube.

12. The system of claim 11, wherein said tube has at least approximately 50 coils.

13. The system of claim 12, wherein each coil has a diameter of approximately 0.5 inches.

14. The system of claim 11, wherein said tube has an inner channel with a diameter of approximately 0.06 inches.

15. A medical cutting system, comprising:
    a handpiece;
    a cutting element attached to said handpiece;
    a tube that is connected to said handpiece and has a length of at least 8 feet; and,
    a pump connected to said tube.

16. A method for performing a medical procedure, comprising:
    placing a medical device at a surgical site;
    irrigating the surgical site with a fluid;
    aspirating the fluid through a tube that has a pre-formed coil;
    creating a fragment with the medical device, wherein the fragment occludes the tube; and,
    clearing the fragment within the tube, wherein the pre-formed coil creates a resistance that minimizes a variation of fluid flow through the tube when the fragment is cleared.

17. The method of claim 16, wherein the fluid is pulled with a vacuum pump.

18. The method of claim 16, wherein the fluid is pulled through a tip of a medical device.

19. A method for performing a medical procedure, comprising:
    placing a medical device at a surgical site;
    irrigating the surgical site with a fluid;
    aspirating the fluid through a tube that is at least 8 feet long;
    creating a fragment with the medical device, wherein the fragment occludes the tube; and,
    clearing the fragment within the tube, wherein the 8 foot tube creates a resistance that minimizes a variation of fluid flow through the tube when the fragment is cleared.

20. The method of claim 19, wherein the fluid is pulled with a vacuum pump.

21. The method of claim 19, wherein the fluid is pulled through a tip of a medical device.

\* \* \* \* \*